US011337867B2

United States Patent
Maki et al.

(10) Patent No.: US 11,337,867 B2
(45) Date of Patent: May 24, 2022

(54) DISPOSABLE WEARING ARTICLE

(71) Applicant: UNICHARM CORPORATION, Shikokuchuo (JP)

(72) Inventors: Hideaki Maki, Kanonji (JP); Takuya Inoue, Kanonji (JP); Yuta Matsushima, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 536 days.

(21) Appl. No.: 16/338,495

(22) PCT Filed: Nov. 21, 2017

(86) PCT No.: PCT/JP2017/041784
§ 371 (c)(1),
(2) Date: Apr. 1, 2019

(87) PCT Pub. No.: WO2018/097123
PCT Pub. Date: May 31, 2018

(65) Prior Publication Data
US 2019/0247242 A1    Aug. 15, 2019

(30) Foreign Application Priority Data

Nov. 22, 2016  (JP) .............................. JP2016-226626
Nov. 20, 2017  (JP) .............................. JP2017-223210

(51) Int. Cl.
*A61F 13/49*     (2006.01)
*A61F 13/496*    (2006.01)
(Continued)

(52) U.S. Cl.
CPC ...... *A61F 13/49061* (2013.01); *A61F 13/496* (2013.01); *A61F 13/49011* (2013.01);
(Continued)

(58) Field of Classification Search
CPC ............ A61F 13/49058; A61F 13/4906; A61F 13/49061; A61F 13/49019; A61F 13/49011
See application file for complete search history.

(56) References Cited

U.S. PATENT DOCUMENTS

2002/0147439 A1* 10/2002 Tanaka .................. A61F 13/496
                                                         604/398
2011/0106039 A1*  5/2011 Saito .................. A61F 13/49019
                                                         604/385.3
(Continued)

FOREIGN PATENT DOCUMENTS

| JP | 2010-82364 A | 4/2010 |
| JP | 2013-138795 A | 7/2013 |
| JP | 2015-516273 A | 6/2015 |

OTHER PUBLICATIONS

International Search Report in PCT Application No. PCT/JP2017/041784, dated Feb. 13, 2018, 4pp.

*Primary Examiner* — Susan S Su
(74) *Attorney, Agent, or Firm* — Hauptman Ham, LLP

(57) ABSTRACT

A disposable wearing article which enables the liquid absorbent structure to fit the body stably, without a shift in position of the waist opening edge part when worn. A liquid absorbent structure further has an end flap positioned between a front-end edge of the liquid absorbent structure and a front-end edge of an absorbent core. A front waist region has a stretchable sheet extending inward in a vertical direction Y from a waist opening edge and overlapping with the end flap, a plurality of waist elastic members extending in a lateral direction X and overlapping with at least the end flap, a first region positioned between the waist opening edge and the front-end edge of the liquid absorbent structure, and a second region including the stretchable sheet and the waist elastic members, at an inner side in the vertical (Continued)

direction Y of the front-end edge of the liquid absorbent structure.

10 Claims, 6 Drawing Sheets

(51) Int. Cl.
  *A61F 13/53* (2006.01)
  *A61F 13/514* (2006.01)
(52) U.S. Cl.
  CPC .. *A61F 13/49012* (2013.01); *A61F 13/49019* (2013.01); *A61F 13/53* (2013.01); *A61F 13/514* (2013.01); *A61F 2013/49052* (2013.01)

(56) References Cited

U.S. PATENT DOCUMENTS

| | | | |
|---|---|---|---|
| 2012/0083757 A1* | 4/2012 | Takahashi | A61F 13/51401 604/370 |
| 2013/0310785 A1 | 11/2013 | Wade et al. | |
| 2014/0288523 A1* | 9/2014 | Hasse | A61F 13/4906 604/385.29 |
| 2014/0358110 A1* | 12/2014 | Takahashi | A61F 13/49058 604/385.29 |

* cited by examiner

DISPOSABLE WEARING ARTICLE

RELATED APPLICATIONS

The present application is a National Phase of PCT/JP2017/041784, filed Nov. 21, 2017, and claims priority based on Japanese Patent Application No. 2016-226626, filed Nov. 22, 2016 and Japanese Patent Application No. 2017-223210, filed Nov. 20, 2017.

TECHNICAL FIELD

The present invention relates to a disposable wearing article.

BACKGROUND

Disposable wearing articles are known having a lateral direction and a vertical direction, and including a front waist region, a rear waist region, a crotch region positioned between the front and rear waist regions, and a liquid absorbent structure having an absorbent core, extending to the front waist region centering the crotch region. For instance, Patent Literature 1 discloses a wearing article including that an outer sheet defining the front waist region has a folding part, and has a part lying on a skin facing surface of the outer sheet, a portion lying on a non-skin facing surface, and a plurality of thread (or string)-like waist elastic members secured between these portions.

CITATION LIST

Patent Literature

[PTL 1]: Japanese Patent Application Laid-open Publication No. 2013-138795

SUMMARY

Technical Problem

In the wearing article disclosed by [PTL: 1], the waist elastic members being secured along a waist opening edge, locations of the waist elastic members are pressed strongly against the skin of a wearer, due to a linear pressure. When the wearer is a young baby, as an abdomen is bulged frontward to be poochy, when the waist opening edge is elongated around the waist, it is partially pressed against by the waist elastic members and without being along the shape of the body of the wearer, and may have a position shift without conforming to the movement of the body. Moreover, it may create a feeling of tightness against the wearer due to the linear pressure of the waist elastic members, and may leave pressure marks on the skin. On the other hand, for fitting the front waist region gently to the skin, when elasticity is imparted only by a stretchable sheet for the whole, the liquid absorbent structure may move upward by the movement of the wearer, and the wearing article may slip down due to a weight after absorbing a body fluid.

An object of the present invention is to provide a disposable wearing article which enables the liquid absorbent structure to fit the body of a wearer stably, without a shift in position of the waist opening edge when worn.

Solution to Problem

The present invention is directed to a disposable wearing article having a vertical direction and a lateral direction, and including a front waist region, a rear waist region, a crotch region extending between the front waist region and the rear waist region, a liquid absorbent structure having an absorbent core, extending to the front waist region centering on the crotch region and the rear waist region, and a waist opening.

In the disposable wearing article according to the present invention, the liquid absorbent structure further has an end flap positioned between a front-end edge of the liquid absorbent structure and a front-end edge of the absorbent core, and the front waist region has a stretchable sheet extending inward in the vertical direction from a waist opening edge and overlapping with the end flap, a plurality of waist elastic members extending in the lateral direction and overlapping with at least the end flap, a first region positioned between the waist opening edge and the front-end edge of the liquid absorbent structure, and a second region including the stretchable sheet and the waist elastic members, at an inner side in the vertical direction of the front-end edge of the liquid absorbent structure.

According to a preferable embodiment of the present invention, a contraction force of the second region is stronger than a contraction force of the first region. The first region gently fits a poochy abdomen of a wearer, and it is possible to fit stably the end flap of the liquid absorbent structure to the body of the wearer at the first region, without giving a feeling of tightness against the wearer and leaving pressure marks on the skin.

According to another preferable embodiment of the present invention, an inner-end edge of the stretchable sheet lies at an outer side in the vertical direction of the front-end edge of the absorbent core. Thus, no gathers due to contraction of the stretchable sheet are formed in the absorbent core, and it is possible to suppress a material cost.

According to still another preferable embodiment of the present invention, the stretchable sheet lies at a non-skin facing surface of the waist elastic members. In this instance, it is possible to give a soft impression of underwear without an outer shape of the waist elastic members appearing on an outer surface of a diaper.

According to still another preferable embodiment of the present invention, the stretchable sheet lies at a skin facing surface of the waist elastic members. Here, it is possible to press the stretchable sheet toward the wearer's skin under the contraction force of the waist elastic members and to suppress the pressure marks due to a linear pressure of the waist elastic members being left on the skin.

According to still another preferable embodiment of the present invention, the front waist region further includes a third region having the waist elastic members disposed therein, and overlapping the absorbent core, and the contraction force of the second region is stronger than a contraction force of each of the first region and the third region. By the front waist region having the third region, it is possible to press the absorbent core against the wearer's skin, and to absorb the body fluid effectively. Moreover, by the second region having the contraction force relatively stronger than the contraction force of the first region and the third region, it is possible to fit stably the end flap of the liquid absorbent structure to the wearer's body.

According to still another preferable embodiment of the present invention, the disposable wearing article further has a waist panel defining the front waist region, and the liquid absorbent structure is disposed on the skin facing surface side of the front waist panel, and an outer-layer sheet lying at a non-skin facing surface side of the waist panel has a cover formed by folding a portion thereof toward the skin facing surface along an outer-end edge of the stretchable sheet, and covering the end flap. Here, the number of sheets layered of the waist opening edge being large, the stiffness becomes relatively high, and even when the liquid absorbent structure is moved upward by the movement of the wearer, the waist opening edge is hardly folded.

According to still another preferable embodiment of the present invention, the front waist panel further includes an inner-layer sheet lying at the skin facing surface, an outer-layer sheet lying at the non-skin facing surface, and an intermediate sheet interposed between the inner and outer layer sheets, and the stretchable sheet and the intermediate sheet are spaced apart from each other in the vertical direction between the inner and outer layer sheets. Thus, it is possible to suppress a local stiffness change due to overlapping of the sheets.

According to still another preferable embodiment of the present invention, the waist elastic members are disposed in a spaced-apart portion between the stretchable sheet and the intermediate sheet. Here, it is possible to suppress change in stiffness and elasticity at the spaced-apart portion of the sheets.

Advantageous Effects of Invention

According to the disposable wearing article according to the present invention, the front waist region is positioned between the waist opening edge and the front-end edge of the liquid absorbent structure, and the overall region thereof gently fits the skin along the shape of the body by the first region in which the stretchable sheet is positioned, thereby making it possible to suppress the shift in position of the waist opening edge part when worn, and no feeling of tightness is given and no pressure marks are left on the skin. Moreover, by the second region including the stretchable sheet and the waist elastic members in the end flap, the liquid absorbent structure is held firmly and suppressed from moving upward, and it is possible to prevent the shift in position of the diaper.

BRIEF DESCRIPTION OF DRAWINGS

The drawings illustrate specific embodiments of the present invention including optional and preferred embodiments as well as essential features of the invention.

DESCRIPTION OF EMBODIMENTS

Figure 1:
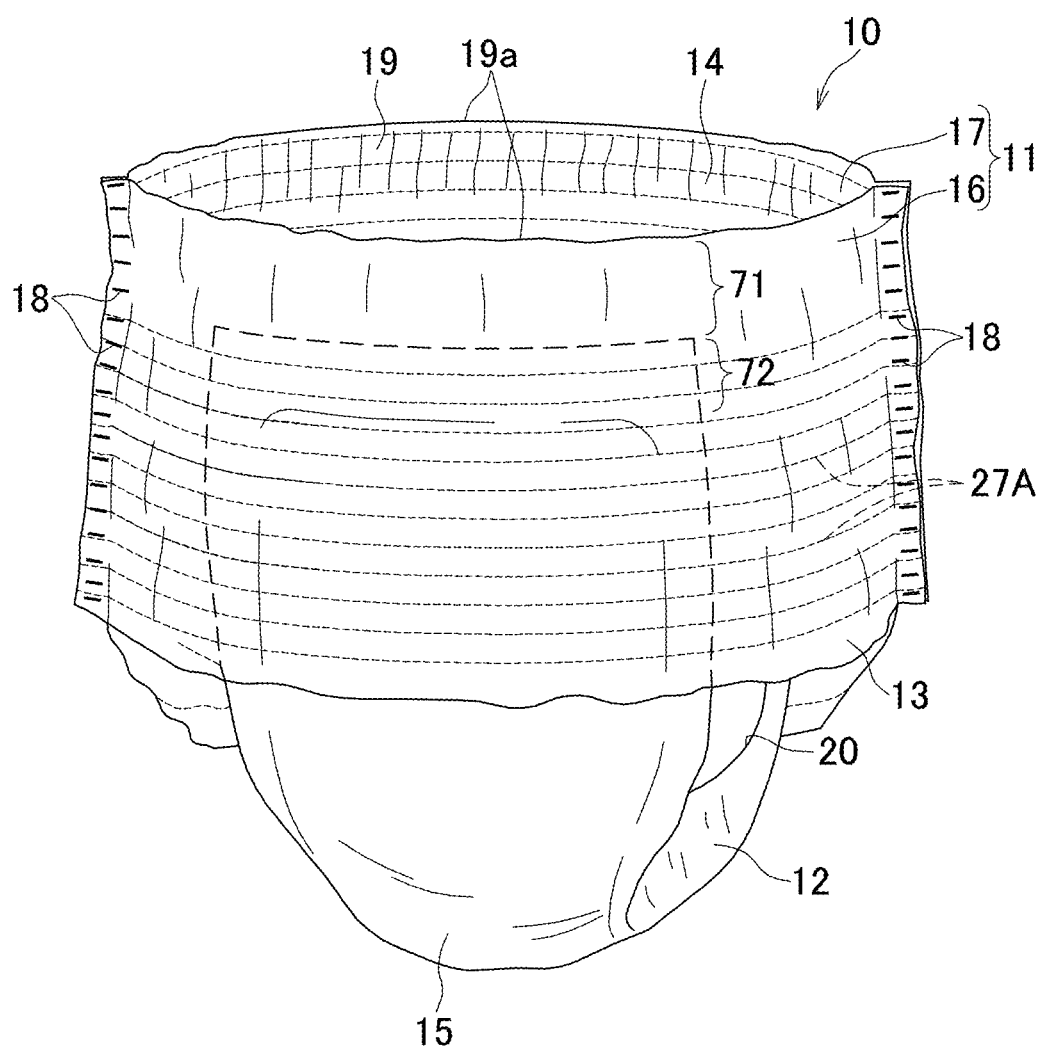
FIG. 1 Perspective view of a disposable wearing article (diaper) according to the present invention.

The embodiments described below relate to a disposable wearing article (disposable diaper) as illustrated in FIGS. 1 through 6, including both optional and preferred features as well as those features which are essential of the invention.

Referring to FIG. 1 to FIG. 6, a disposable diaper 10 illustrated as an example of the disposable wearing article of the present invention has a lateral direction X and a vertical direction Y orthogonal to each other, and a direction of thickness Z, as well as a skin facing surface and a non-skin facing surface positioned on an opposite side of the skin facing surface, and includes an annularly-shaped elastic waist panel 11 extending in a direction around the waist, a liquid absorbent structure (absorbent chassis) 12 fixed to a skin facing surface of the elastic waist panel 11, a front waist region 13, a rear waist region 14, and a crotch region 15 positioned between the front waist region 13 and the rear waist region 14.

The elastic waist panel 11 has a function of an elastic belt stretchable in the direction around the waist, and includes a front waist panel 16 defining the front waist region 13 and a rear waist panel 17 defining the rear waist region 14.

The front waist panel 16 has a substantially rectangular shape contoured by an inner-end edge 16a, an outer-end edge 16b, and side edges 16c, 16d extending from the inner-end edge 16a up to the outer-end edge 16b. The rear waist panel 17 has a substantially trapezoidal shape contoured by an inner-end edge 17a, an outer-end edge 17b, first side edges (side edges of the rear waist region) 17c, 17d extending in the vertical direction Y from the outer-end edge 17b, and second side edges 17e, 17f extending obliquely inward in the vertical direction from the both first side edges 17c, 17d.

A waist opening 19 and a pair of leg openings 20 are respectively defined by both side edges of the front waist panel 16 and both side edge of the rear waist panel 17 facing each other, being overlapped with each other, and being connected by side seams 18 continually in the vertical direction Y. The side seams 18 are formed by various thermal welding means such as heat embossing/debossing and ultrasonic processing.

The front and rear waist panels 16, 17 include inner-layer sheets 21, 22 lying on the skin facing surface, and outer-layer sheets 23, 24 lying on the non-skin facing surface, respectively.

For the inner and outer layer sheets 21 to 24, materials such as SMS (spun bonded/melt-blown/spun bonded) fibrous nonwoven fabrics having a mass in a range of 10 to 30 g/m$^2$, spun-bonded fibrous nonwoven fabrics, air-through fibrous nonwoven fabrics, or plastic sheets, porous plastic sheets, and laminated sheets thereof, may be used.

The outer-layer sheets 23, 24 have body parts 23a, 24a positioned on the non-skin facing surface, extended parts 23b, 24b extending outward in the vertical direction Y from the body parts 24a, 24b, and defining a portion of the skin facing surface, folded parts 23c, 24c positioned between the body parts 23a, 24a and the extended parts 23b, 24b.

The front waist panel 16 has a stretchable sheet 30 lying between the inner-layer sheet 21 and the body part 23a of the outer-layer sheet 23. The stretchable sheet 30 extends from the waist opening edge 19a toward the crotch region 15.

For the stretchable sheet 30, stretchable fibrous nonwoven fabrics manufactured by various known manufacturing methods, such as, spun-bonded nonwoven fabrics made of elastic fibers having a mass in a range of 10 to 40 g/m$^2$, and more preferably 15 to 30 g/m$^2$, air-through fibrous nonwoven fabrics, and needle-punched nonwoven fabrics may be used. Elastic fibers using a thermoplastic elastomer and rubber as a raw material may be used. In particular, when a thermoplastic elastomer is used as a raw material, melt-spinning using an extruder similarly as for a usual thermoplastic resin is possible, or fibers achieved in such manner are easy to adhere by fusion melting, and are suitable as stretchable fibrous nonwoven fabrics. The stretchable sheet 30 may not be a sheet having elasticity in only one direction (lateral direction), and may be a sheet having elasticity in two or more than two directions (lateral direction and vertical direction). An elongation rate of the stretchable sheet 30 in the lateral direction is 1.2 to 3.0 times, and is 2.5 times in a specific embodiment.

The front waist region 13 has an intermediate sheet 38 positioned between the inner-layer sheet 21 and the body part 23*a* of the outer-layer sheet 23, in the direction of thickness Z. The rear waist panel 17 has an intermediate sheet 39 lying between the inner-layer sheet 22 and the body part 24*a* of the outer-layer sheet 24, in the direction of thickness Z.

The intermediate sheets 38, 39 are formed of liquid-impermeable fibrous nonwoven fabrics, and liquid-impermeable and moisture-impermeable plastic films, or a laminated sheet thereof. A graphic element visible from exterior of the diaper 10 may be disposed on the intermediate sheets 38, 39. The graphic element may be an element such as various known decorative patterns, pictures, characters, symbols, and/or coloring.

Figure 4:
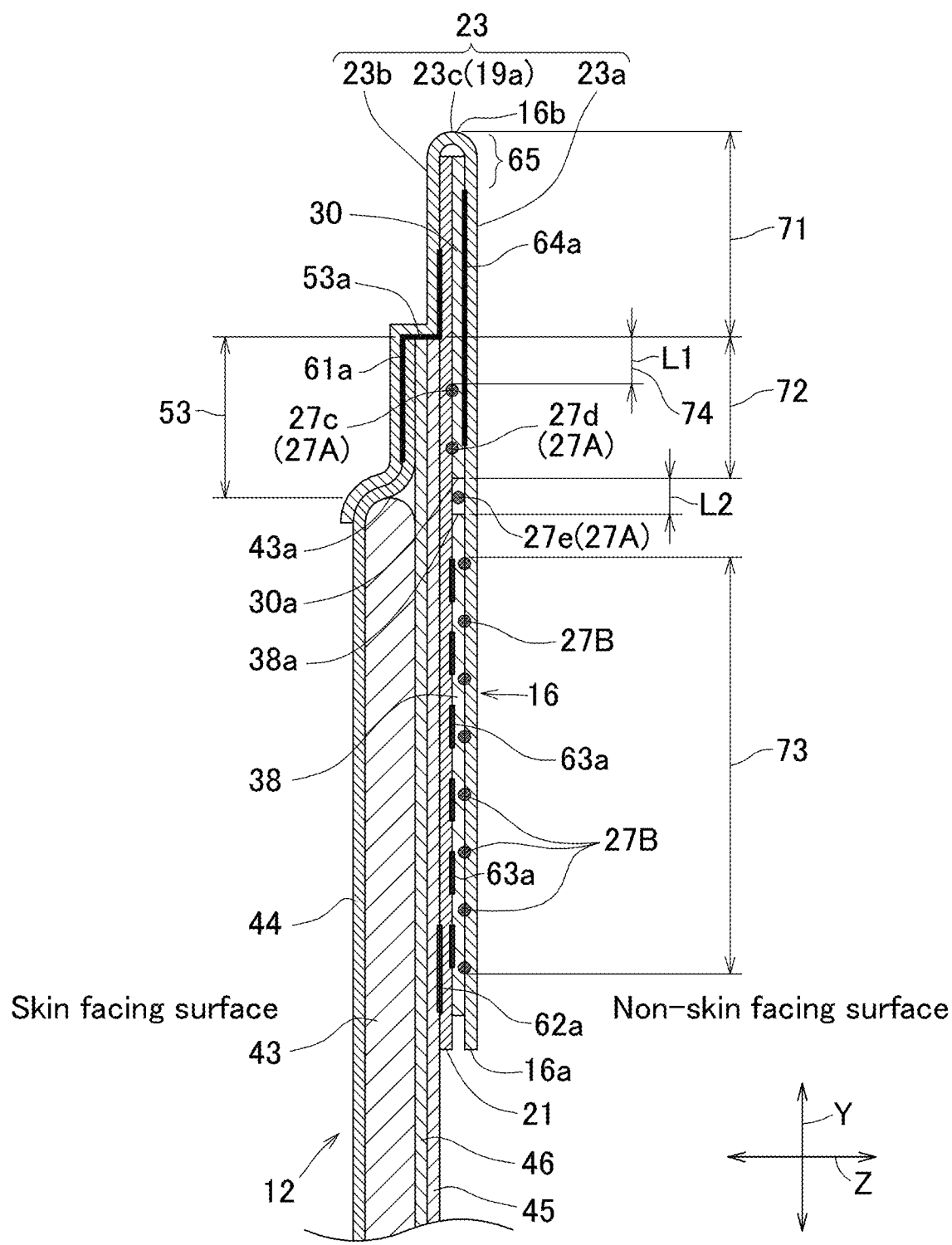
FIG. 4 Cross-sectional view along line IV-IV shown in FIG. 3.

Referring to FIG. 4, the stretchable sheet 30 and the intermediate sheet 38 are disposed in the vertical direction Y of the front waist region 13 such that an inner-end edge 30*a* of the stretchable sheet 30 and an outer-end edge 38*a* of the intermediate sheet 38 are spaced apart. More specifically, in the vertical direction Y, the inner-end edge 30 of the stretchable sheet 30 and the outer-end edge 38*a* of the intermediate sheet 38 are disposed to have a spaced-apart dimension L2. The spaced-apart dimension L2 is preferably 1.0 to 15.0 mm for example, and 5.0 to 10.0 mm more preferably.

Between the inner-layer sheets 21, 22 and the outer-layer sheets 23, 24 of the front and rear waist panels 16, 17, a plurality of front waist elastic members (waist elastic members) 27 and thread (or string) or ribbon-like rear waist elastic members 28 are stretchably disposed in the lateral direction X, and the front and rear waist panels 16, 17 are elasticized at least in the lateral direction X.

The front waist elastic members 27 include a plurality of upper front waist elastic members 27A extending in the lateral direction to overlap with the stretchable sheet 30, and a plurality of lower front waist elastic members 27B extending in the lateral direction not to overlap with the stretchable sheet 30 at a lower side of the upper front waist elastic members 27A. The rear front elastic members 28 include upper rear waist elastic members 28A extending in the lateral direction X along the waist opening edge 19*a*, and lower rear waist elastic members 28B extending in the lateral direction X between the upper rear waist elastic 28A and the inner-end edge 17*a*.

Figure 5:
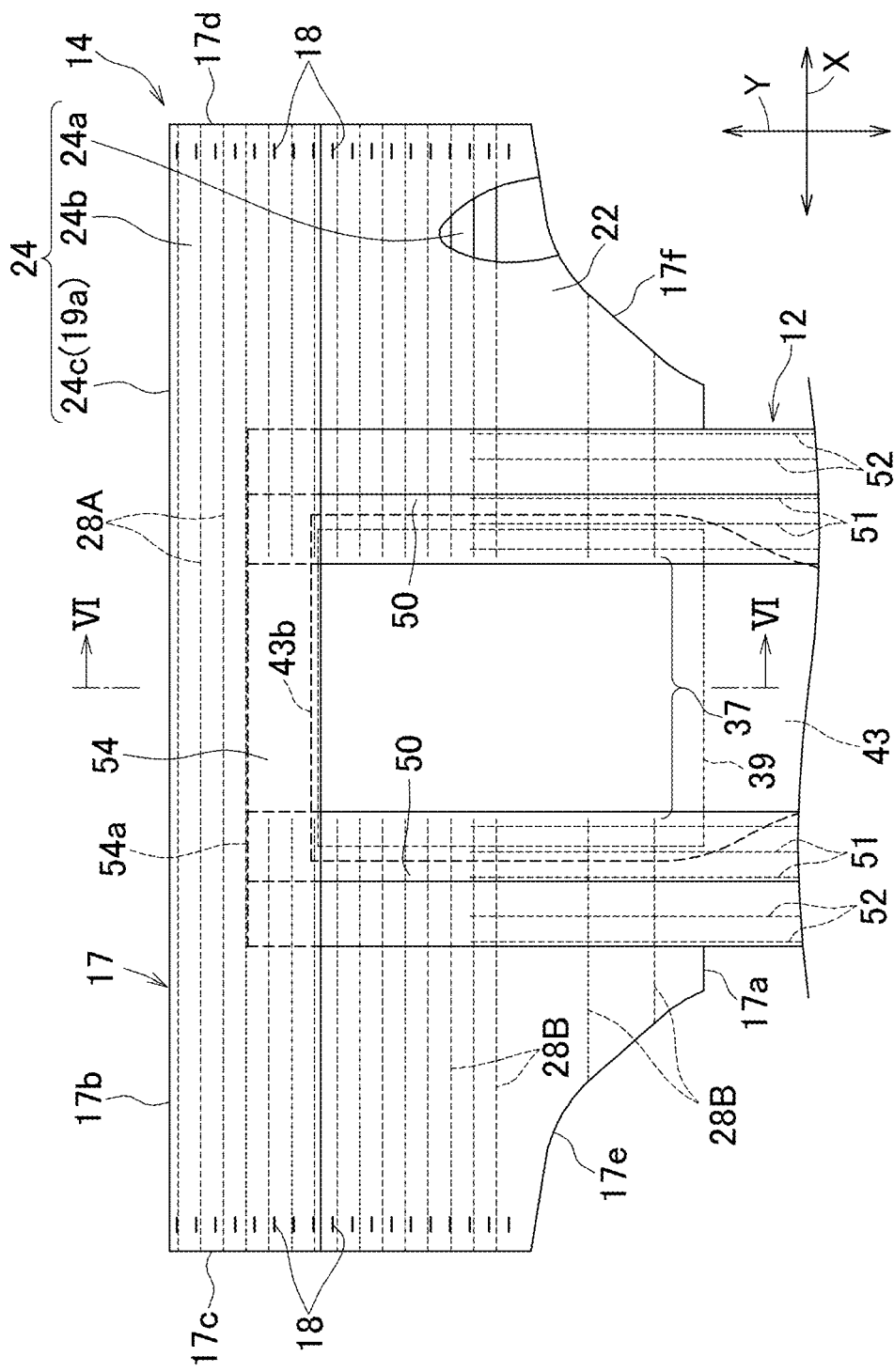
FIG. 5 Enlarged view of a rear waist region.

Referring to FIG. 5, a portion of the lower rear waist elastic members 28B, at a middle part of the rear waist region 14 is either cut or removed, and a rear non-stretchable region 37 is defined. In such manner, the non-stretchable region 37 being positioned at the middle part of the rear waist region 14, a contraction force of the lower rear waist elastic members 28B acts directly on a middle part of the liquid absorbent structure 12 (middle part of the absorbent core 43) positioned on an inner surface of the rear waist panel 17 preventing the formation of gathers, and it is possible to suppress a degradation of absorption performance due to the contraction force acting thereon.

As the front waist elastic members 27 and the rear waist elastic members 28, thread (or string)- or ribbon-like elastic materials having fineness in a range of 350 to 1240 dtex disposed in a state of being elongated 1.5 to 3.5 times may be used. It is possible to change appropriately conditions such as the fineness, the elongation rate, and the spaced-apart dimension (pitch) between the two elastic members of the front waist elastic members 27 and the rear waist elastic members 28, and for the disposable wearing article (diaper) to be worn stably on the body of the wearer, it is preferable to set the conditions of the elastic members such that a stretching force of a stretchable region by the upper front and rear waist elastic members 27A, 28A becomes stronger than a stretching force of a stretchable region by the lower front and rear elastic members 27B, 28B.

Referring to FIG. 4, in the front waist region 13, out of the upper front waist elastic members 27A, an upper front waist elastic 27*c* positioned nearest to the waist opening edge 19*a* is positioned to be spaced-apart face-to-face in the vertical direction from the front-end edge 53*a* of the liquid absorbent structure 12. In the present embodiment, the upper front elastic members 27A and the front-end edge 53*a* of the liquid absorbent structure 12 are spaced apart by a spaced-apart dimension L1. The spaced-apart dimension L1 is 1.0 to 20.0 mm, and preferably 5.0 to 10.0 mm.

Unlike an example in the diagram, two or more than two upper front waist elastic members 27A may be disposed in a front-end flap 53, and the upper front waist elastic members 27A may be disposed near the front-end edge 53*a* of the liquid absorbent structure 12. In this case, the spaced-apart dimension L1 is not formed, but it is possible to suppress a shift in position of the liquid absorbent structure 12 by enhancing the contraction force of the overall front-end flap 53.

In a portion having a spaced-apart dimension L2 positioned between the intermediate sheet 38 and the stretchable sheet 30 of the front waist region 13, or in other words, between the inner-end edge 30*a* of the stretchable sheet 30 and the outer-end edge 38*a* of the intermediate sheet 38, an upper front waist elastic 27*e* positioned nearest to the crotch region 15 in the upper front waist elastic members 27A is positioned.

A hot-melt adhesive is not applied to inner surfaces of the inner and outer layer sheets 21, 23 of the front waist region 13 and the inner and outer layer sheets 22, 24 of the rear waist region 14, and excluding a joining portion by the side seams 18, the inner and outer layer sheets are joined to each other only through an adhesive such as the hot-melt adhesive applied to the front waist elastic members 27 and the rear waist elastic members 28. It is preferable that the hot-melt adhesive is applied to a portion facing the inner and outer layer sheets 21 to 24 throughout the entire periphery of the front waist elastic members 27 and the rear waist elastic members 28.

Figure 2:
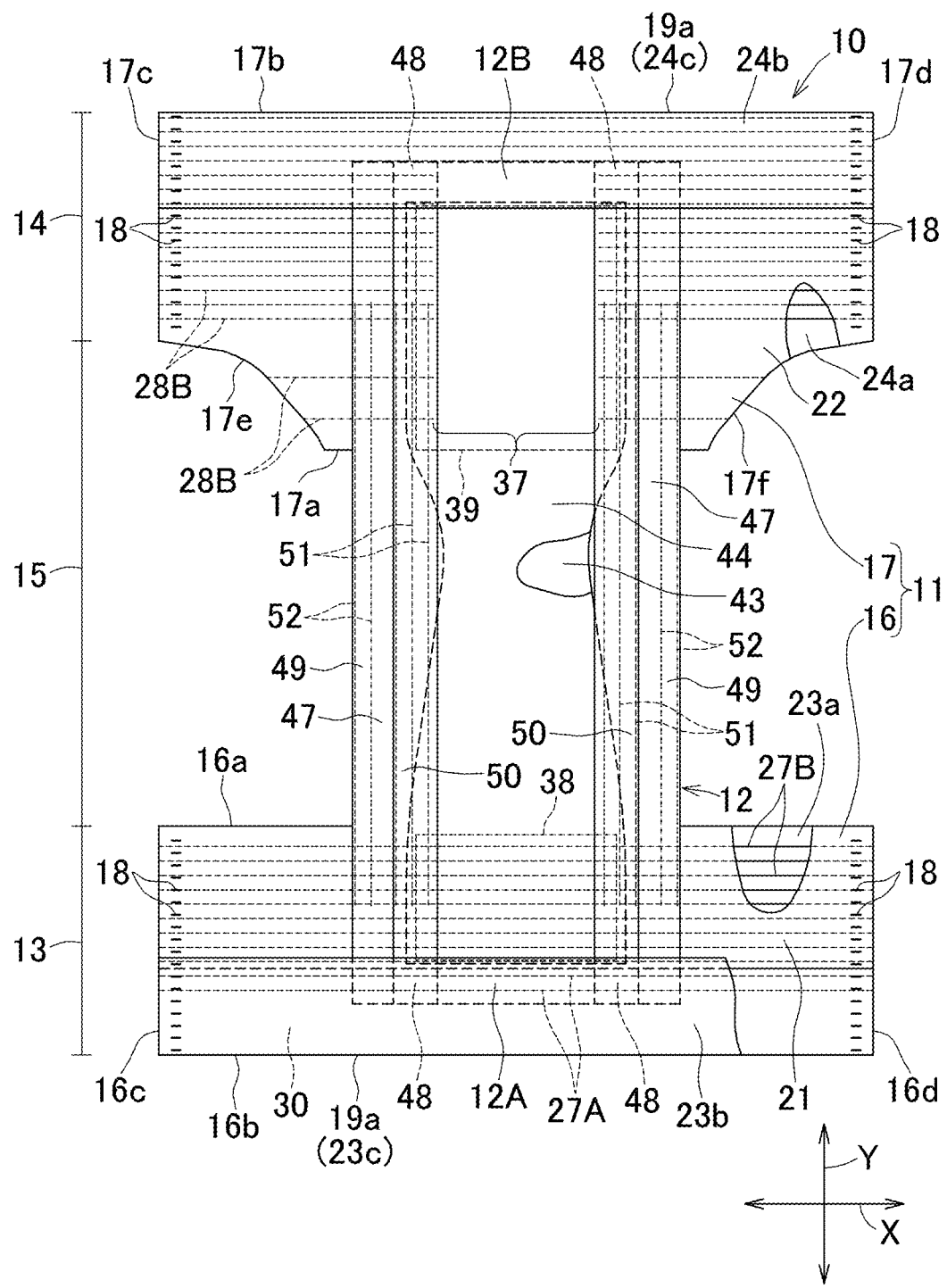
FIG. 2 Partially cut-away view of an unfolded diaper in a state in which elastic members are extended in a vertical direction and a lateral direction of the diaper.

Referring to FIG. 2 and FIG. 4, the liquid absorbent structure 12 includes front and rear ends 12A, 12B fixed to the skin facing surface of the front and rear waist panels 16, 17, the absorbent core 43 extending in the vertical direction Y at least in the crotch region 15, a body-side liner (top sheet) 44 which is liquid permeable and is formed of hydrophilic fibrous nonwoven fabrics lying on the skin facing surface side of the absorbent core 43, a back sheet 45 formed of hydrophobic or liquid hardly-permeable fibrous nonwoven fabrics lying on the non-skin facing surface side of the absorbent core 43, and a leakage barrier sheet (leakage barrier film) 46 which is liquid impermeable having a size covering the an overall surface of at least the absorbent core 43 facing the back sheet 45, and disposed between the absorbent core 43 and the back sheet 45. For the body-side liner 44 and the back sheet 45, various known fibrous nonwoven fabrics such as SMS (spun bonded/melt-blown/spun bonded) fibrous nonwoven fabrics and spun-bonded nonwoven fabrics may be used.

The absorbent core 43 is formed of a material in which a required amount of super absorbent polymer particles and fluff pulp are mixed, and is semi-rigid having a relatively higher rigidity than that of sheet members such as the inner and outer layer sheets 21 to 24 forming the diaper 10. Moreover, a middle part in the vertical direction Y of the absorbent core 43 is in the form of a panel having a narrow shape, and the whole of it is wrapped in a liquid diffusion sheet such as tissue.

The body-side liner 44 and the back sheet 45 are extended from an outer peripheral edge of the absorbent core 43. The liquid absorbent structure 12 has a pair of side flaps formed by the body-side liner 44 and the back sheet 45 extending outward in the lateral direction from both side edges of the absorbent core 43, and the front-end flap (end flap) 53 and a rear-end flap 54 extending in the lateral direction outboard of the vertical direction of the front and rear end edges of the absorbent core 43.

The back sheet 45 has both side parts 47 positioned outboard of the lateral direction X from both side edges of the leakage barrier sheet 46. Both side parts 47 are positioned at both side edges of the leakage barrier sheet 46 and are folded toward the skin facing surface side along folding lines extending in the vertical direction Y, and fixed to the body-side liner 44. Both side parts 47 have both end fixing parts 48 spaced apart from each other in the vertical direction, a proximal edge part 49 fixed to both side edge parts of the body-side liner 44 and both side edge parts of the leakage barrier sheet 46, and a distal edge part (free edge part) 50 extending in the vertical direction between both end fixing parts and extending in the vertical direction in parallel to the proximal edge part 49.

The distal edge part 50 has a shape of a sleeve formed by folding and fixing an outer edge part of the back sheet 45, and a plurality of string- or strand-like cuff elastic members 51 extending in the vertical direction is fixed contractibly under tension at an interior of the sleeve. The distal edge part 50 is fixed through fixing parts positioned at both ends in the vertical direction in a state of being collapsed toward outboard of the lateral direction. By the cuff elastic 51 being contracted, the distal edge part 50 forms a leakage barrier cuff on the body side of the wearer from the body-side liner 44, and prevents leakage of body exudates by fitting the thighs of the wearer. A plurality of string- or strand-like leg elastic members 52 extending in the vertical direction Y is contractibly fixed in stretched form to both side parts 47 of the back sheet 45 outboard in the lateral direction of the leakage barrier cuff.

Figure 6:
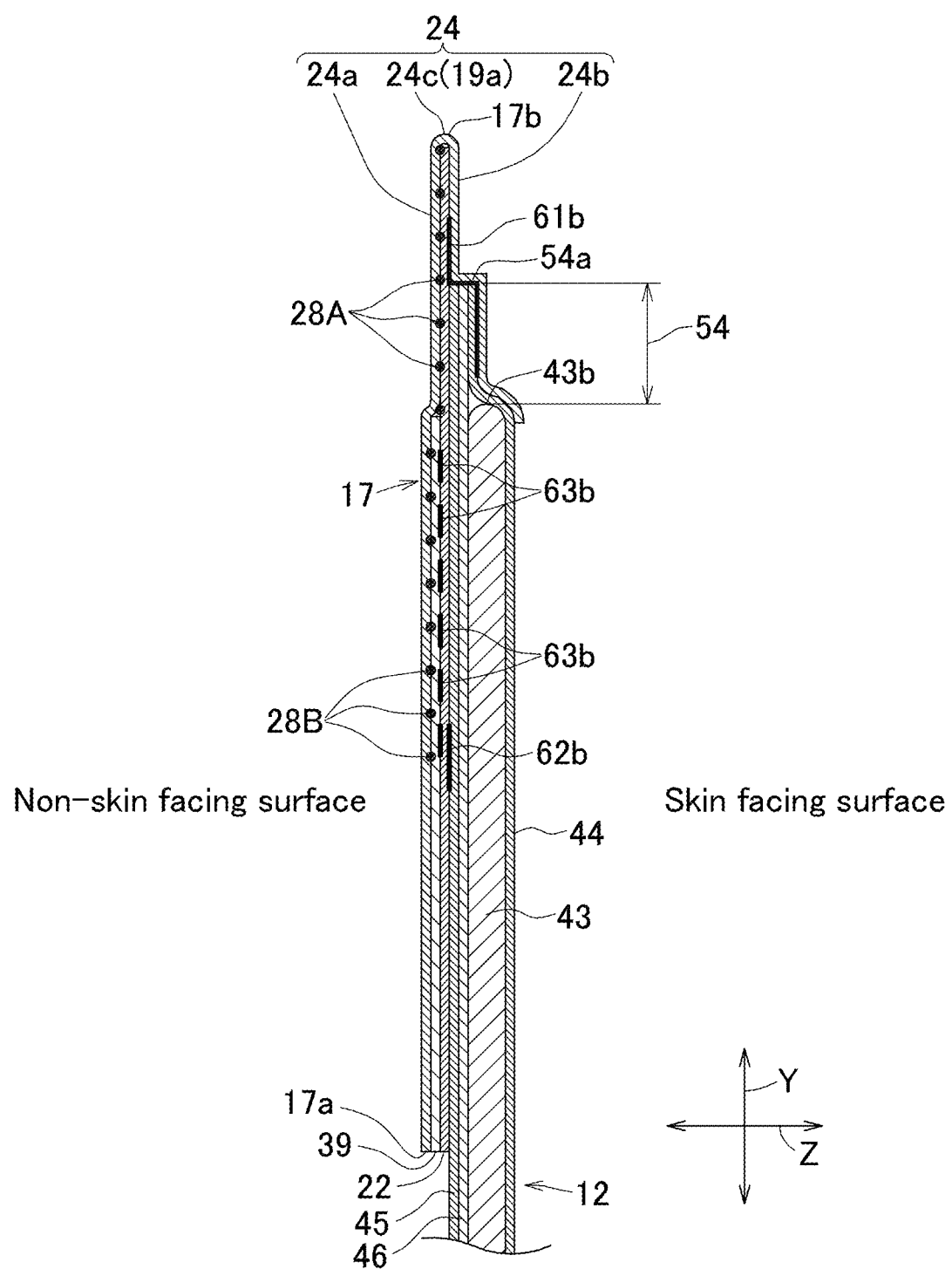
FIG. 6 Cross-sectional view along line VI-VI shown in FIG. 5.

Referring to FIG. 4 and FIG. 6, the extended parts 23b, 24b of the outer-layer sheets 23, 24 and the liquid absorbent structure 12 are fixed by joining parts 61a, 61b having an adhesive such as a hot-melt adhesive applied to inner surfaces thereof. The liquid absorbent structure 12 and the inner and outer layer sheets 21, 22 are fixed by fixing parts 62a, 62b having an adhesive such as a hold-melt adhesive applied to inner surfaces thereof. The inner-layer sheets 21, 22 and the intermediate sheets 38, 39 are fixed by fixing parts 63a, 63b having an adhesive such as a holt-melt adhesive applied to inner surfaces thereof. In the front waist region 13, the stretchable sheet 30 and the body part 23a of the outer-layer sheet 23 are fixed by a fixing part 64a having an adhesive such as a hot-melt adhesive applied to inner surface thereof. A non-fixing region 65 having no fixing part 64a therein is positioned at the waist opening edge 19a of the front waist region 13.

Figure 3:
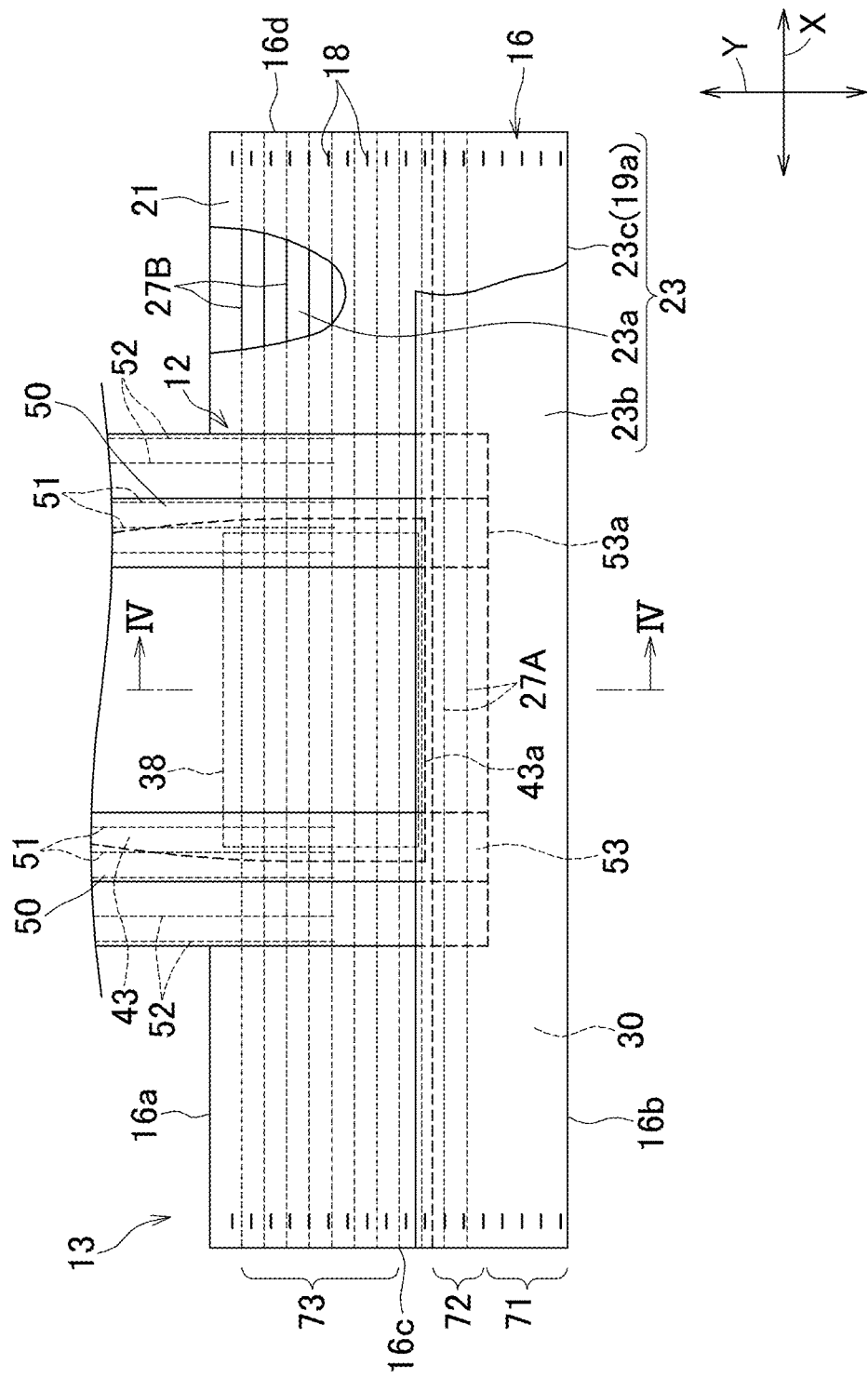
FIG. 3 Enlarged view of a front waist region.

Referring to FIG. 3 and FIG. 4, the front waist region 13 has a first region (first elastic region) 71 positioned between the waist opening edge 19a and the front-end edge 53a of the liquid absorbent structure 12, and a second region (second elastic region) 72 including the stretchable sheet 30 and the upper front waist elastic members 27A, positioned at the front-end flap 53, or in other words, at an inner side in the vertical direction of the front-end edge 53a. By the stretchable sheet 30 being positioned in the first region 71, and the stretchable sheet 30 and the upper front waist elastic members 27A being partially overlapped, a contraction force of the second region 72 is stronger than that of the first region 71. Thread (or string)- or ribbon-like elastic members may be disposed in the first region 71 in so far as the contraction force of the second region 72 becomes stronger than the contraction force of the first region 71.

In the diaper 10 according to the present embodiment, the first region 71 having a relatively weaker contraction force including the stretchable sheet 30 being positioned at the waist opening edge part, the waist opening edge part is elongated (stretched) in a direction around the waist along a shape of an abdomen of a young baby having a shape bulged frontward, and it is possible to prevent a shift in position due to the movement of the body of the wearer when worn. Moreover, by the front waist elastic members 27 not being disposed, it does not create a feeling of tightness against the wearer and leaves no pressure marks on the skin which is caused due to a linear pressure of the front waist elastic members 27. Moreover, the second region 72 having the contraction force stronger than the contraction force of the first region 71 being positioned at the front-end flap 53 of the front waist region 13, the diaper 10 is held firmly, and the front-end flap 53 stably fits a lower abdomen of the wearer, and the liquid absorbent structure 12 does not move upward due to the movement of the wearer, or does not slip down due to the weight after absorbing the body fluids.

The second region 72 has a spaced-apart portion 74 positioned between the front-end edge 53a of the liquid absorbent structure 12, the upper front waist elastic 27c positioned nearest to the waist opening edge 19a, which is one of the upper front waist elastic members 27A. The second region 72 being positioned at the front-end edge flap 53, the number of sheets layered therein is more than that in the first region 71, and a stiffness of the second area 72 is higher than a stiffness of the first area 71. Moreover, since an elastic member is not disposed in the spaced-apart portion 74 in the second area 72, stiffness thereof is lowered than that of a portion in which the upper front waist elastic members 27c, 27e are disposed. Therefore, the spaced-apart portion 74 is positioned as a buffer region for suppressing a steep change in the stiffness between the first region 71 and the portion in which the upper front waist elastic members 27c, 27e are disposed, and formation of an unevenness near the front-end edge 53a of the liquid absorbent structure 21 due to steep change in the stiffness is suppressed, thereby making it possible to suppress the waist opening edge part being spaced apart from the body by being folded at the stage difference.

The inner-end edge 30a of the stretchable sheet 30 is positioned outboard (upper side) in the vertical direction of the front-end edge 43a of the absorbent core 43. By the stretchable sheet 30 not being positioned to be overlapping with the absorbent core 43, it is possible to suppress formation of gathers that may lower an absorbability in the absorbent core 43 by a contraction effect of the stretchable sheet 30. Moreover, by disposing the stretchable sheet 30 only at the waist opening edge part, it is possible to reduce the waste of material, and to suppress the material cost.

The stretchable sheet 30, at the front waist panel 16, is interposed between the inner-layer sheet 21 and the outer-layer sheet 23, and the upper front waist elastic members 27A are positioned between the stretchable sheet 30 and the inner-layer sheet 21. By the stretchable sheet 30 being positioned on the non-skin facing surface of the upper front waist elastic members 27A, an outer shape of the upper front waist elastic members 27A does not appear on an outer surface of the front waist panel 16, and it is possible to give an appearance of an underwear.

Whereas, unlike the example shown in the diagram, the stretchable sheet 30 may be positioned on the skin facing surface of the upper front waist elastic members 27A. In this instance, it is possible to press the stretchable sheet 30 toward the skin by the contraction force of the waist elastic members, and to suppress the pressure marks due to the linear pressure of the waist elastic members from being left on the wearer's skin.

The liquid absorbent structure 12 is positioned on the skin facing surface of the front waist panel 16, and the extended part (cover portion) 23b formed by the outer-layer sheet 23 being folded toward the skin facing surface along the outer-end edge of the inner-layer sheet 21 covers the front-end flap 53, and is fixed to the inner-layer sheet 21 and the front-end flap 53 through the joining parts 61a. By the outer-layer sheet 23 being folded (returned) at the waist opening edge part, and the extended part 23b being overlapped with the front-end flap 53 of the liquid absorbent structure 12, the number of sheets layered becomes larger, and the stiffness of the waist opening edge becomes relatively higher. Accordingly, even when the wearer raises legs and the liquid absorbent structure 12 moves upward, it is possible to prevent the waist opening edge part from being folded and having a shift in position near the front-end edge 53a of the liquid absorbent structure 12.

The intermediate sheet 38 and the stretchable sheet 30 are positioned to be spaced-apart face-to-face in the vertical direction between the inner and outer layer sheets 21, 23 of the front waist panel 16. By the intermediate sheet 28 and the stretchable sheet 30 not overlapping each other, it is possible to suppress a steep change in the stiffness and an unevenness created due to overlapping of the intermediate sheet 28 and the stretchable sheet 30.

The upper front waist elastic 27e is disposed in a spaced-part portion of (between) the stretchable sheet 30 and the intermediate sheet 38. By disposing the upper front waist elastic 29e in a portion where both the sheets 30, 38 do not exist, it is possible to suppress the steep change in the stiffness and an unevenness in this portion, and to suppress lifting-off and deformation of the front-end flap 53. The upper front waist elastic 27e being positioned near the front-end edge 43a of the absorbent core 43, it is possible to press a vicinity of the front-end edge 43a on the skin by the contraction force.

The non-fixing region 65 in which the sheets 21, 23, and 30 are not joined to each other is positioned at the waist opening edge 19a of the front waist panel 16. By the non-fixing region 65 being positioned in the waist opening edge 19a, the stiffness is lowered compared to the case in which the fixing part 64a is positioned, and the wearer does not feel pain even when the skin makes a contact with the waist opening edge 19a.

Referring to FIG. 4, the front waist region 13 further includes a third region (third elastic region) 73 having an elasticity in the lateral direction X, and positioned at a lower side of the second region 72, in which the lower front waist elastic members 27B are disposed. The front waist region 13, by having the third region 73, is capable of absorbing effectively the body fluids by pressing the absorbent core 43 toward the skin. A contraction force at a predetermined width of the second region 72 is stronger than a contraction force at predetermined widths of the first region 71 and the third region 73 respectively.

The contraction force (tensile stress) of the predetermined width in the lateral direction of the front waist region 13, is specifically 0.01 to 0.04 N/mm for the first region 71, 0.05 to 0.10 N/mm for the second region 72, and 0.01 to 0.04 N/mm for the third region 73. Furthermore, in a specific embodiment, a width (length dimension in the vertical direction) of the first region 71 being 25 mm and the contraction force being 0.389 N, the contraction force per unit length (width) is 0.016 N/mm, and a width (length dimension in the vertical direction) of the second region 72 being 20 mm and the contraction force being 0.893 N, the contraction force per unit length (width) is 0.045 N/mm, and a width (length dimension in the vertical direction) of the third region 73 being 60 mm and the contraction force being 1.378 N, the contraction force per unit length (width) is 0.022 N/mm.

Measurement Method for First to Third Regions

For measurement of the contraction force of the first to third regions 71 to 73, Autograph type tensile tester (such as AG-1KN1) manufactured by Shimadzu Seisakusho Co., Ltd. (Shimadzu Corporation) was used. Firstly, for the diaper 10 in a state of being elongated (stretched) to an extent such that the gathers due to the contraction effect of the elastic members have disappeared from the surface thereof, after measuring a dimension (initial dimension) in the lateral direction X between the inner edges of the side seams 18 in the front and rear waist regions 13, 14, both side edge parts including the side seams 18 of the diaper 10 were cut, and each of the regions 71 to 73 was cut out by a cutter from the portion toward the front waist region 13, and was let to be a sample.

At the time of selecting the regions 71, 73 from the front waist region 13, a portion on the waist opening edge 19a side upon cutting along the front-end edge (first cutting line) of the liquid absorbent structure 12 was let to be the first region 71, a portion cut out by further cutting along the inner-end edge 30a (second cutting line) of the stretchable sheet 30 was let to be the second region 72, and the remaining portion was let to be the third region 73.

Next, one end of each sample was pinched in a fixed chuck and the other end thereof was pinched in a movable chuck, and upon turning over (reversing) after elongating (stretching) to approximately 90% size of an initial dimension at a velocity 300 mm/min, a tensile load when made to contract to 75% size of the initial dimension was calculated, and a value converted to a stress value (N/mm) per unit width (mm) was let to be the contraction force.

It is preferable that the elongation rate of the upper front waist elastic members 27c, 27d of the upper front waist elastic members 27A is smaller than the elongation rate of the lower front waist elastic members 27B. The upper front waist elastic members 27c, 27d are not overlapped with the semi-rigid absorbent core 43, and the elongation is not inhibited, but the elastic members 27B being overlapping with the absorbent core 43, the elongation thereof is degraded. Therefore, when the elastic members 27c, 27d, and 27B have an equal elongation rate, a difference may arise in the degree of elongation, but setting the elongation rate of the upper front waist elastic members 27c, 27d relatively smaller, it is possible to let the elastic members 27c, 27d, and 27B be elongated in a balanced manner.

It is preferable to set appropriately the fineness, the elongation rate, and the spaced-apart dimension (pitch) between the elastic members of the upper rear waist elastic members 28A such that the contraction force of the waist opening edge part in the rear waist region 14 facing the front waist region 14 becomes stronger than the contraction force of the front waist region 14 on the waist opening edge 19a side, or in other words, the contraction force of the first region 71. In such manner, by making the contraction force on the rear waist opening edge part side stronger compared to the contraction force of the front waist opening edge part side, it does not create a feeling of tightness against the wearer, and by the rear waist opening edge, it is possible to fit the rear waist region 14 stably to a posterior part of the wearer.

As materials forming the diaper 10, unless specified clearly in particular, apart from the materials mentioned in the present description (specification), known materials that are used commonly in this sort of field can be used without restriction. Moreover, the terms such as 'the first', 'the second', and 'the third' used in the present description are used solely for distinguishing similar components and positions etc.

REFERENCE SIGNS LIST 10 disposable diaper (disposable wearing article)
12 liquid absorbent structure
13 front waist region
14 rear waist region
15 crotch region
19 waist opening
19a waist opening edge
21 inner-layer sheet
23 outer-layer sheet
27 front waist elastic (waist elastic)
27A upper front waist elastic
27B lower front waist elastic
30 stretchable sheet
30a inner-end edge of stretchable sheet
38 intermediate sheet
43 absorbent core
43a front-end edge
44 body-side liner (inner-surface sheet)
45 back sheet (outer-surface sheet)
53 end flap (front-end flap)
53a front-end edge
71 first region
72 second region
73 third region
X lateral direction
Y vertical direction

The invention claimed is:

1. A disposable wearing article having a vertical direction and a lateral direction, comprising:
a front waist region;
a rear waist region;
a crotch region extending between the front waist region and the rear waist region;
a liquid absorbent structure having an absorbent core, extending to the rear waist region centering on the crotch region; and
a waist opening, wherein
the liquid absorbent structure further includes an end flap positioned between a front-end edge of the liquid absorbent structure and a front-end edge of the absorbent core,
the front waist region includes
a stretchable sheet extending in the vertical direction from the waist opening edge towards the crotch region and overlapping with the end flap, and
a plurality of waist elastic members overlapping with at least the end flap and extending in the lateral direction,
the front waist region has
a first region positioned between the waist opening edge and the front-end edge of the liquid absorbent structure, and
a second region including the stretchable sheet and one or more waist elastic members among the plurality of waist elastic members, the second region positioned below the front-end edge of the liquid absorbent structure in the vertical direction, and
the stretchable sheet includes a lower end edge positioned above the front-end edge of the absorbent core in the vertical direction.

2. The disposable wearing article according to claim 1, wherein a contraction force of the second region is stronger than a contraction force of the first region.

3. The disposable wearing article according to claim 1, wherein the stretchable sheet is positioned at a non-skin facing surface of the plurality of waist elastic members.

4. The disposable wearing article according to claim 1, wherein the stretchable sheet is positioned at a skin facing surface of the plurality of waist elastic members.

5. The disposable wearing article according to claim 1, wherein
the front waist region further includes a third region having further one or more waist elastic members among the plurality of waist elastic members disposed therein, and the third region overlapping the absorbent core, and
a contraction force of the second region is stronger than a contraction force of each of the first region and the third region.

6. The disposable wearing article according to claim 1, further comprising:
a front waist panel defining the front waist region, wherein
the liquid absorbent structure is disposed on a skin facing surface of the front waist panel,
the stretchable sheet includes an upper end edge opposite to the lower end edge of the stretchable sheet in the vertical direction,
an outer-layer sheet lying at a non-skin facing surface of the front waist panel has a cover formed by folding a portion thereof toward the skin facing surface along said upper end edge of the stretchable sheet, and
the cover covers the end flap.

7. The disposable wearing article according to claim 1, further comprising:
a front waist panel defining the front waist region, wherein
the front waist panel further has
an inner-layer sheet lying at a skin facing surface of the front waist panel,
an outer-layer sheet lying at a non-skin facing surface of the front waist panel, and
an intermediate sheet interposed between the inner layer sheet and the outer layer sheet, and the stretchable sheet and the intermediate sheet are spaced apart from each other in the vertical direction between the inner and outer layer sheets.

8. The disposable wearing article according to claim 7, wherein the plurality of waist elastic members are disposed in a spaced-apart portion between the stretchable sheet and the intermediate sheet.

9. A disposable wearing article having a vertical direction and a lateral direction, comprising:
a front waist region;
a rear waist region;
a crotch region extending between the front waist region and the rear waist region;
a liquid absorbent structure having an absorbent core, extending to the rear waist region centering on the crotch region; and
a waist opening, wherein
the liquid absorbent structure further includes an end flap positioned between a front-end edge of the liquid absorbent structure and a front-end edge of the absorbent core,
the front waist region includes
  a stretchable sheet extending in the vertical direction from the waist opening edge towards the crotch region and overlapping with the end flap, and
  a plurality of waist elastic members overlapping with at least the end flap and extending in the lateral direction,
the front waist region has
  a first region positioned between the waist opening edge and the front-end edge of the liquid absorbent structure, and
  a second region including the stretchable sheet and one or more waist elastic members among the plurality of waist elastic members, the second region positioned below the front-end edge of the liquid absorbent structure in the vertical direction, and
the stretchable sheet is positioned at a non-skin facing surface of the plurality of waist elastic members.

10. A disposable wearing article having a vertical direction and a lateral direction, comprising:
a front waist panel defining a front waist region;
a rear waist region;
a crotch region extending between the front waist region and the rear waist region;
a liquid absorbent structure having an absorbent core, extending to the rear waist region centering on the crotch region; and
a waist opening, wherein
the liquid absorbent structure further includes an end flap positioned between a front-end edge of the liquid absorbent structure and a front-end edge of the absorbent core,
the front waist region includes
  a stretchable sheet extending in the vertical direction from the waist opening edge towards the crotch region and overlapping with the end flap, and
  a plurality of waist elastic members overlapping with at least the end flap and extending in the lateral direction,
the front waist region has
  a first region positioned between the waist opening edge and the front-end edge of the liquid absorbent structure, and
  a second region including the stretchable sheet and one or more waist elastic members among the plurality of waist elastic members, the second region positioned below the front-end edge of the liquid absorbent structure in the vertical direction,
the front waist panel further has
  an inner-layer sheet lying at a skin facing surface of the front waist panel,
  an outer-layer sheet lying at a non-skin facing surface of the front waist panel, and
  an intermediate sheet interposed between the inner layer sheet and the outer layer sheet, and
the stretchable sheet and the intermediate sheet are spaced apart from each other in the vertical direction between the inner and outer layer sheets.

* * * * *